United States Patent [19]
Grabowski et al.

[11] Patent Number: 5,641,347
[45] Date of Patent: Jun. 24, 1997

[54] BARIUM-FREE DENTAL GLASS HAVING GOOD X-RAY ABSORPTION

[75] Inventors: Danuta Grabowski, Taunusstein; Marc Clement, Mainz; Johann Daimer, Oberahrain; Hartmut Paschke, Ergolding, all of Germany

[73] Assignee: Schott Glaswerke, Mainz, Germany

[21] Appl. No.: 556,811

[22] Filed: Nov. 2, 1995

[30] Foreign Application Priority Data

Dec. 5, 1994 [DE] Germany ............... 44 43 173.2

[51] Int. Cl.⁶ .................... C03C 3/076; A61K 6/02
[52] U.S. Cl. ............... 106/35; 501/55; 501/57; 501/65; 501/66; 501/67; 501/68; 501/69; 501/63; 501/64; 523/116; 523/117; 433/228.1
[58] Field of Search ............... 501/55, 57, 65, 501/66, 67, 68, 69, 63, 64; 106/35; 523/116, 117; 433/228.1

[56] References Cited

FOREIGN PATENT DOCUMENTS

| | | |
|---|---|---|
| 0468435 | 1/1992 | European Pat. Off. . |
| 0622342 | 11/1994 | European Pat. Off. . |
| 2511361 | 2/1983 | France . |
| 3248357 | 7/1984 | Germany . |
| 246288 | 6/1987 | Germany . |
| 3743609 | 7/1988 | Germany . |
| 3939831 | 6/1990 | Germany . |
| 4119483 | 12/1992 | Germany . |
| 4323143 | 12/1994 | Germany . |
| 9418134 | 8/1994 | WIPO . |

OTHER PUBLICATIONS

Database WPI, Section Ch, Week 9030; Derwent Publications Ltd. London, GB; AN 90–226842 XP 02000305 & JP–A–02 153 839 (Nippon Electric Glass); 13 Jun. 1990.

Patent Abstracts of Japan, vol. 016, No. 581 (C–1012), Dec. 21, 1992 & JP–A–04 231060 (Nippon Electric Glass Co Ltd), Aug. 19, 1992.

Patent Abstracts of Japan, vol. 017, No. 627 (C–1131), Nov. 19, 1993 & JP–A–05 194130 (Hoya Corp), Aug. 3, 1993.

Patent Abstracts of Japan, vol. 017, No. 627 (C–1131), Nov. 19, 1993 & JP–A–05 194132 (Morita Mfg Co Ltd), Aug. 3, 1993.

*Primary Examiner*—Karl Group
*Attorney, Agent, or Firm*—Felfe & Lynch

[57] ABSTRACT

Disclosed is a barium-free glass of good x-ray absorption, which has a composition (in wt.-% on the oxide basis) of $SiO_2$ 50–75; $ZrO_2$ 5–30; $Li_2O$ 0–5; $Na_2O$ 0–25; $K_2O$ 0–25; $\Sigma$ alkali oxides 0–25. Preferred is a dental glass of the composition of $SiO_2$ 55–70; $ZrO_2$ 10–25; $Li_2O$ 0–15; $Na_2O$ 10–25; $K_2O$ 0–15; $\Sigma$ alkaloids 15–25. The glass can furthermore contain also up to 3 wt.-% of fluorine, up to 5 wt.-% of MgO, up to 5 wt.-% of $TiO_2$, and in each case up to 10 wt.-% of the oxides $Al_2O_3$, $GeO_2$, $P_2O_5$, $La_2O_3$, $Y_2O_3$, $Ta_2O_3$, $Gd_2O_3$, ZnO and $Nb_2O_5$. The glass finds its use in powder form with an average particle size of $\leq 10$ μm as filler for dental composites for filling teeth.

22 Claims, No Drawings

BARIUM-FREE DENTAL GLASS HAVING GOOD X-RAY ABSORPTION

BACKGROUND OF THE INVENTION

Dental composites are being used increasingly for filling teeth, in order to circumvent possible side-effects of amalgam fillings, and in order to achieve a better aesthetic appearance. Dental composites consist as a rule of an inorganic material and an organic synthetic resin binder. The inorganic content consists mostly of glass powder. The glass powder must satisfy certain requirements as to the physical and chemical properties of the glass to be used for the powder in addition to the qualities necessary for a good filling.

The glass powder must first have a high strength. Also, the index of refraction of the filling must be matched to that of the synthetic resin in order to assure that the tooth filling will satisfy the aesthetic requirements, i.e., that it will be scarcely distinct from the dental enamel. It is furthermore important that the thermal expansion of the glass in the range in which the filling is used, i.e., at temperatures between 30° C. and 70° C., will match that of the substance of the tooth, so as to assure that the filling will have a sufficient resistance to temperature changes. The danger is precisely that the alternation between cold and hot foods might destroy its integrity. A minimal coefficient of expansion is commonly sought, because the comparatively high thermal expansion of the synthetic resin binder can thereby be compensated.

Furthermore, the tooth filling must be clearly distinct in its x-ray image from that of the tooth material. This signifies that the glass must have a certain minimum of x-ray opacity. According to ISO 4049: 1988 (E) the x-ray opacity of a filling of a thickness of 2 mm must be greater than that of an aluminum plate of equal thickness. The x-ray opacity of the filling is expressed as the aluminum equivalent thickness. The aluminum equivalent thickness is understood as the thickness of an aluminum plate which has the same x-ray absorption as a plate of filling material 2 mm thick. An aluminum equivalent thickness of 3 accordingly means that a 2 mm thick filling produces the same absorption as an aluminum plate 3 mm thick.

Also, the glass powder should be chemically stable against water, acids and alkalies to contribute to a long life of the filling. Due to possible toxic side effects, the use of barium components in the glass is avoided, although these components produce good x-ray opacity. The use of components containing lead is fundamentally forbidden for reasons of toxicity.

A fluoroaluminum silicate glass powder for use in dentistry is disclosed in U.S. Pat. No. 4,775,592. The basic glasses for this powder however have a very poor crystallization stability, so that their production is very difficult. The glasses have a very high fluorine content of about 10 to 40 wt-% and to achieve sufficient hardness and chemical stability they must contain $Al_2O_3$ in amounts of up to 40% by weight. Even then, the hydrolytic stability of the glass powder is not satisfactory.

Furthermore, a barium-free dental glass with a high x-ray absorption is disclosed in the older German patent application P 43 23 143.7, and has a composition in percentage by weight of oxides of $SiO_2$ 45–65%; $B_2O_3$ 5–20%; $Al_2O_3$ 5–20%; CaO 0–10%; SrO 15–35% and $F_2O$ 0–2%. The good x-ray opacity is achieved here by a comparatively high content of SrO.

An object of the invention is to provide a dental glass having a good x-ray absorption, which is free of barium and lead, and which has a good chemical and thermal stability.

THE INVENTION

This purpose is accomplished by a dental glass which is a barium-free dental glass having a good x-ray absorption and which on the oxide basis, in wt.-% comprises:

| | |
|---|---|
| $SiO_2$ | 50–75 |
| $ZrO_2$ | 5–30 |
| $Li_2O$ | 0–5 |
| $Na_2O$ | 0–25 |
| $K_2O$ | 0–25 |
| Σ alkali oxides | 0–25 |

The glass can be built up of a minimal number of components, which considerably facilitates the toxicological judgment of the glass for possible side effects.

$SiO_2$ in amounts of 50–75 wt.-% and $ZrO_2$ in amounts of 5–30 wt.-% are used as glass making components. If the $ZrO_2$ content increases to more than 30%, the melting of these glasses becomes very difficult and thus the cost of producing such glasses is very high. $ZrO_2$ contents of 10–25 wt.-% are used preferentially. Due to the zirconium content the mechanical properties, especially the tensile and compressive strength, are decidedly improved and the brittleness of the glass is reduced. The $SiO_2$ content is to be between 50 and 75 wt.-%, with an $SiO_2$ content of 55 to 70 wt.-% being preferred. To facilitate the melting of the $SiO_2/ZrO_2$ glass, alkali oxides in the form of 0–25 wt.-% of $Na_2O$, 0–25 wt.-% of $K_2O$ and/or 0–5 wt.-% of $Li_2O$ can be added. If the content of the alkali oxides exceeds 25 wt.-%, the chemical and mechanical stability of the glass is diminished and the coefficient of expansion definitely increases. The preferred content of $Na_2O$ is between 10 and 25 wt.-%, that of $K_2O$ between 0 and 15 wt.-% and $Li_2O$ between 0 and 5, while the total content of the alkali oxides is preferably between 15 and 25 wt.-%. With this alkali content the glass is easily melted and has good chemical stability.

For the correction of the index of refraction, the addition of up to 3 wt.-% of fluorine is advantageous. The glass can furthermore contain up to 10 wt.-% of CaO. CaO can be added to the glass to vary the physical characteristics of the glass. CaO contributes, for example, to raising the aluminum equivalent thicknesses. In comparison to Si, calcium has about 3 times the mass attenuation coefficient. Higher percentages of CaO result in the impairment of the x-ray absorption of the glass and an increased tendency to devitrification.

Without substantially impairing the properties of the glass, the glass may also contain up to 10 wt.-% of SrO, up to 5 wt.-% of MgO, up to 10 wt.-% of $Al_2O_3$, up to 10 wt.-% of $GeO_2$, up to 10 wt.-% of $P_2O_5$, up to 5 wt.-% of $TiO_2$, and up to 10 wt.-% in each case of $La_2O_3$, $Y_2O_3$, $Ta_2O_3$, $Gd_2O_3$, ZnO, $B_2O_3$, $Nb_2O_5$ and $P_2O_5$. The number of the additional oxides present in the glass should not, however, be made so high as to lose sight of the aim of facilitating the toxicological judgment of the glass.

To match the optical properties of the filling insofar as possible to the tooth enamel, the index of refraction of the glass is adapted to that of the synthetic resin. Synthetic resins used have refractive indexes ranging from 1.5 to 1.6. The glass according to the invention has a refractive index of less than 1.6 and thus satisfies this requirement.

In the practice of dentistry the ease of detecting the filling in the x-ray photograph is of great importance. Fillings made with the glass according to the invention have an aluminum thickness equivalent of >2.5 mm, generally >3 mm, and thus have the properties required for use in tooth restoration. The aluminum thickness equivalent is understood as the thickness of an aluminum plate which has the same x-ray absorption as a filling 2 mm thick.

After the glass is manufactured, the glass is used in a known manner for making a glass powder, for example by grinding and if necessary screening. Screening produces a glass powder which has an average particle size of <10 µm, and preferably 0.5 to 5 µm. The grain size of the powder is important and affects the possibility of polishing the composite, as well as the composite's resistance to abrasion and its mechanical strength. To obtain good mechanical properties it is desirable, as usual, to have an excessively narrow grain size distribution, such as achieved by conventional grinding and screening out the coarse particles. A maximum particle size of 40 µm, preferably 20 µm and most preferably 10 µm should not be exceeded. In this form the glass powder is particularly suitable for use as a filler for dental composites used as dental fillings.

It is quite common to silanize the glass powders used as fillers for dental composites, silanization being well known both in itself and for this purpose. Silanization facilitates achieving a high degree of fill in the composite and has a favorable influence on the mechanical properties of the composite.

To prepare a dental composite useful as a dental filling, the glass powder is mixed with a hardenable synthetic resin of the type commonly used in dentistry. Ultraviolet-hardening resins on a basis of acrylate, methacrylate, 2,2-bis-[4-(3-methacryloxy-2-hydroxypropoxy)-phenyl]-propane-(bis-GMA), urethane-methacrylate, alkanediolmethacrylate or cyanoacrylate can be used. The glass powder used as filling is present in the finished synthetic resin pastes in proportions of up to 80 wt.-% For reasons of strength an effort is made to make the glass powder content as high as possible.

EXAMPLES 6 glasses are melted from commonly available, pure raw materials whose composition and properties are listed in the table. The index of refraction was measured at a wavelength ($n_d$) of 587 nm, and the aluminum equivalent thickness (AG) according to ISO 4049.

TABLE

| Glass examples (composition data in wt.-%) | | | | | | |
| --- | --- | --- | --- | --- | --- | --- |
|  | 1 | 2 | 3 | 4 | 5 | 6 |
| $SiO_2$ | 65,7 | 64,0 | 55,0 | 63,0 | 70,0 | 65,0 |
| $ZrO_2$ | 10,0 | 16,0 | 20,0 | 12,0 | 5,0 | 25,0 |
| $Na_2O$ | 24,3 | 20,0 | 25,0 | 15,0 | 25,0 | 10,0 |
| CaO |  |  |  |  |  |  |
| $n_d$ | 1,5300 | 1,5478 | 1,5681 | 1,5606 | 1,5133 | 1,5665 |
| AG (mm) | 2,8 | 3,8 | 4,6 | 3,3 | 2,5 | 4,9 |

It will be understood that the specification and examples are illustrative but not limitative of the present invention and that other embodiments within the spirit and scope of the invention will suggest themselves to those skilled in the art.

What is claimed is:

1. A barium-free dental glass powder having an average particle size of ≦40 µm and a good x-ray absorption wherein said glass, on an oxide basis, in wt.-% comprises:

| $SiO_2$ | 50–75 |
| --- | --- |
| $ZrO_2$ | 5–30 |
| $Li_2O$ | 0–5 |
| $Na_2O$ | 0–25 |
| $K_2O$ | 0–25 |
| Σ alkali oxides | 0–25, | said dental glass having a refractive index of 1.5 to 1.6.

2. The dental glass powder of claim 1 in wt.-% comprising:

| $SiO_2$ | 55–70 |
| --- | --- |
| $ZrO_2$ | 10–25 |
| $Li_2O$ | 0–5 |
| $Na_2O$ | 10–25 |
| $K_2O$ | 0–25 and |
| Σ alkali oxides | 10–25. |

3. The dental glass powder of claim 1 further comprising a content of CaO in an amount of up to 10 wt.-% and an $F_2$ content of up to 3 wt.-%.

4. The dental glass powder of claim 2 further comprising a content of CaO in an amount of up to 10 wt.-% and an $F_2$ content of up to 3 wt.-%.

5. The dental glass powder of claim 1, in wt.-%, further comprising:

| SrO | 0–10 |
| --- | --- |
| MgO | 0–5 |
| $Al_2O_3$ | 0–10 |
| $GeO_2$ | 0–10 |
| $P_2O_5$ | 0–10 |
| $TiO_2$ | 0–5 |
| $La_2O_3$ | 0–10 |
| $Y_2O_3$ | 0–10 |
| $Ta_2O_3$ | 0–10 |
| $Gd_2O_3$ | 0–10 |
| ZnO | 0–10 |
| $B_2O_3$ | 0–10 |
| $Nb_2O_5$ | 0–10 and |
| $P_2O_5$ | 0–10. |

6. The dental glass powder of claim 2, in wt.-%, further comprising:

| SrO | 0–10 |
| --- | --- |
| MgO | 0–5 |
| $Al_2O_3$ | 0–10 |
| $GeO_2$ | 0–10 |
| $P_2O_5$ | 0–10 |
| $TiO_2$ | 0–5 |
| $La_2O_3$ | 0–10 |
| $Y_2O_3$ | 0–10 |
| $Ta_2O_3$ | 0–10 |
| $Gd_2O_3$ | 0–10 |
| ZnO | 0–10 |
| $B_2O_3$ | 0–10 |
| $Nb_2O_5$ | 0–10 and |
| $P_2O_5$ | 0–10. |

7. The dental glass powder of claim 1 having an aluminum equivalent thickness of ≧2.5 mm.

8. The dental glass powder of claim 2 having an aluminum equivalent thickness of ≧2.5 mm.

9. The dental glass powder of claim 1 wherein the $ZrO_2$ content is ≧12 to about 30 wt.-%.

10. The dental glass powder of claim 9 wherein Σ alkali oxides is 15 to 25 wt.-% and the zirconium oxide content is between 12 and 25 wt.

11. The dental glass powder of claim 1 wherein the powder has an average particle size of $\leq 20$ μm.

12. The dental glass powder of claim 11 wherein the powder has an average particle size of $\leq 10$ μm.

13. A dental filling composition comprising: a mixture of a synthetic resin and a dental glass powder having an average particle size of $\leq 40$ μm and a good x-ray absorption wherein the glass, on an oxide basis, in wt.-% comprises:

| | |
|---|---|
| $SiO_2$ | 50–75 |
| $ZrO_2$ | 5–30 |
| $Li_2O$ | 0–5 |
| $Na_2O$ | 0–25 |
| $K_2O$ | 0–25 |
| Σ alkali oxides | 0–25. |

14. The dental filling composition of claim 13 wherein the glass has a refractive index $n_d$ of 1.5 to 1.6.

15. The dental filling composition of claim 14 wherein the dental glass has an aluminum equivalent thickness of $\geq 2.5$ mm.

16. The dental filling composition of claim 13 wherein the dental glass has an average particle size of $\leq 10$ μm.

17. The dental filling composition of claim 13 wherein the $ZrO_2$ content of the glass is $\geq 12$ to about 30 wt.-%.

18. A method of making a dental filling composite comprising: mixing a synthetic resin with a dental glass powder having an average particle size of $\leq 40$ μm and a good x-ray absorption wherein the glass, on an oxide basis, in wt.-% comprises:

| | |
|---|---|
| $SiO_2$ | 50–75 |
| $ZrO_2$ | 5–30 |
| $Li_2O$ | 0–5 |
| $Na_2O$ | 0–25 |
| $K_2O$ | 0–25 |
| Σ alkali oxides | 0–25. |

19. The method of claim 18 wherein the dental glass powder has an average particle size of $\leq 20$ μm.

20. The method of claim 18 wherein the dental glass has a refractive index $n_d$ of 1.5 to 1.6.

21. The method of claim 19 wherein the dental glass powder has an average particle size of $\leq 10$ μm.

22. The method of claim 18 wherein the $ZrO_2$ content of the glass is $\geq 12$ to about 30 wt.-%.

* * * * *